(12) United States Patent
Nam

(10) Patent No.: US 10,993,468 B2
(45) Date of Patent: May 4, 2021

(54) COMPOSITION FOR RELIEVING HANGOVERS

(71) Applicant: Jong-hyun Nam, Gangwon-do (KR)

(72) Inventor: Jong-hyun Nam, Gangwon-do (KR)

( * ) Notice: Subject to any disclaimer, the term of this patent is extended or adjusted under 35 U.S.C. 154(b) by 0 days.

(21) Appl. No.: 16/324,538

(22) PCT Filed: Oct. 24, 2016

(86) PCT No.: PCT/KR2016/011950
§ 371 (c)(1),
(2) Date: Feb. 8, 2019

(87) PCT Pub. No.: WO2018/030581
PCT Pub. Date: Feb. 15, 2018

(65) Prior Publication Data
US 2019/0166896 A1    Jun. 6, 2019

(30) Foreign Application Priority Data

Aug. 9, 2016 (KR) .................. 10-2016-0100998

(51) Int. Cl.
| | | |
|---|---|---|
| *A61K 36/185* | (2006.01) | |
| *A23L 33/105* | (2016.01) | |
| *A23L 2/38* | (2021.01) | |
| *A23L 2/52* | (2006.01) | |
| *A23L 2/02* | (2006.01) | |
| *A23L 2/39* | (2006.01) | |
| *A61K 36/73* | (2006.01) | |

(52) U.S. Cl.
CPC ............... *A23L 33/105* (2016.08); *A23L 2/02* (2013.01); *A23L 2/38* (2013.01); *A23L 2/39* (2013.01); *A23L 2/52* (2013.01); *A61K 36/185* (2013.01); *A61K 36/73* (2013.01); *A23V 2002/00* (2013.01); *A23V 2200/334* (2013.01); *A23V 2250/21* (2013.01)

(58) Field of Classification Search
None
See application file for complete search history.

(56) References Cited

U.S. PATENT DOCUMENTS

2007/0065394 A1* 3/2007 Pinney ............... A61K 8/33
424/74

FOREIGN PATENT DOCUMENTS

| KR | 10-0181168 | 2/1999 |
|---|---|---|
| KR | 0181168 B1 | 2/1999 |
| KR | 100406822 B1 | 11/2003 |
| KR | 20100080972 A | 7/2010 |
| KR | 20110022882 A | 3/2011 |
| KR | 101101759 B1 | 1/2012 |
| KR | 101665584 B1 | 10/2016 |

OTHER PUBLICATIONS

Raskin et al. (2004) Current Pharmaceutical Design, 10: 3419-3429. (Year: 2004).*
Revilla et al. (1998) J. Agric. Food Chem. 46: 4592-4597. (Year: 1998).*
"Efficacy and Administration Method of *Corylus heterophylla* Fisher nut", Naver Blog, Oct. 17, 2014, URL: http://blog.naver.com/hebavepo/220153519449, with English Translation.
International Search Report, dated Mar. 20, 2017 for corresponding International Application No. PCT/KR2016/011950 with English translation.
Written Opinion of the ISA, dated Mar. 20, 2017 for corresponding International Application No. PCT/KR2016/011950.
Korean Council for University of Medicine, "Health Functional Food", published May 10, 2009, pp. 146, 168, 171, with partial English translation (9 pages total).
Naver Blog, "Effects and Taking Method of Corylus heterophylla Fisher nut", URL:https://blog.naver.com/hebavepo/220153519449, Oct. 17, 2014, with partial English translation (3 pages total).
Encyclopedia of Science Publishing Company, "Components and Applications of Medicinal Herbs", published Jun. 10, 1999, pp. 6, 169, 364, 365; 96-97, 100-101, 109-110, 113, 115-118, 122-123, 127, 129-131, 137, 144-147, 150-151, 161, 163-164, 169-171, 175-176, 179, 183-184, 186-187, 191-193, 198-203, 205-207, 209-211, 214-215, 219, 226, 232-236, 240, 242-243, 246-251, 256-258, 268, 272, 277, 282-284. 290, 292-293, 295, 301-3302, 307, 313-314, 316, 322-327, 331-332, 334-336, 338-340, 342, 346-348, 351, 352, 354, 355, 363, 365-367, 370, 376-377, 382-387, 393-394, 398, 401, 404-405, 411, 416, 417, 425-428, 441-444, 456, 465-466, 468-469, 471-474, 478-479, 486-488, 492-497, 499-505, 507, 513, 515, 517, 521-524, 528, 531, 532, 535, 537, 541-542, 547-548, 550, 552-553, 563, 567, 569-572, 584-588, 596, 601-606, 609-612, 617-621, 626-631, 634-643, 653-654, 656-657, 659-660, 665, 667-670, 678-679, 681, 683-684, 686, 690-699, 703-708, 713, 716-720, 722-724, 726, 733-739, 741-743, 747, 750, 752-754, 757-759, 761-764, 766, 768, 772-773, 776-778, 780, 782-782, 786, 790-795, 802-807, 809, 811-813, 819, 825, 828-832, 836-839, with partial English translation and Summary (354 pages total).
Nam, Jong Hyun, Kangwon National University, Agricultural Biotechnology College, Food and BioTechnology Dept. "Last Research Report", Jul. 2016, with partial English translation (3 pages total).
GC Pharma, "Written Request for Inspection to Green Cross Corp.", 2016, with English translation of title (3 pages total).
Bu Il Seo et al., "Medicinal Herbology", 2012, preface page, with partial English translation (5 pages total).

(Continued)

*Primary Examiner* — Russell G Fiebig
(74) *Attorney, Agent, or Firm* — Intellectual Property Law Group LLP

(57) ABSTRACT

Provided is a composition for relieving a hangover including as its active ingredients *Corylus heterophylla* Fisher nut extract, *Alnus japonica* Steud. stem extract and *Sorbus commixta* fruit extract. It is verified the composition for relieving a hangover according to the present disclosure reduces blood alcohol concentration more significantly than the composition for relieving a hangover including as its active ingredients *Alnus japonica* Steud. extract and *Sorbus commixta* extract as disclosed in Korean Patent Registration No. 181168 in in vivo tests (including animal testing and human experiment) and that has effects of considerably alleviating various hangover symptoms.

1 Claim, No Drawings

(56) References Cited

OTHER PUBLICATIONS

Yeong-Chul Park et al., "Pharmalogical Effects and Toxicity of Licorice", J. Toxicol. Pub. Health, vol. 18, No. 3, pp. 301-309, 2002, with English Abstract (9 pages total).
Chun-Soo Na et al., "Hepatoprotective and Blood Alcohol Lowering Effects of Fruit Peduncle Extract of *Hovenia dulcis* var. Koreana in the in Vitro and in Vivo Animal Models", J. Pharm. Soc. Korea vol. 48, No. 1, Feb. 11, 2004, pp. 34-40, with English Abstract (7 pages total).
Jong-Min Kim et al., "Protective Effect of Mixed Extract including *Hovenia dulcis* Thunberg against Chronic Ethanol Treatment-induced Cytotoxicity in a Brain and Liver Tissue", Journal of Agriculture & Life Science 50(2), pp. 125-138, Mar. 3, 2016, with English Abstract (14 pages total).
Korea Economic Daily, "Dawn 808, Outstanding Effectiveness for Relieving a Hangover, Growing by 30% a year", Mar. 22, 2010, with English translation of title (2 pages total).
Daily Cho-Sun, "Dawn 808, Necessity for Drinkers, Solving a Hangover Completely", Dec. 12, 2012, with English translation of title (2 pages total).
Daily Cho-Sun, "Dawn 808, Solving heartburn, headache after drinking completely at one go", Sep. 10, 2018, with English translation of title (2 pages total).
Daily Cho-Sun, "Dawn 808, Solving heartburn, headache after drinking completely by adding new patented components", Jan. 21, 2019 with English translation of title (2 pages total).

\* cited by examiner

COMPOSITION FOR RELIEVING HANGOVERS

CROSS-REFERENCE TO RELATED APPLICATIONS

This application is a U.S. National Phase application, under 35 U.S.C. § 371, of International Application no. PCT/KR2016/011950, with an international filing date of Oct. 24, 2016, and claims benefit of Republic of Korea Application no. 10-2016-0100998 filed on Aug. 9, 2016, which are hereby incorporated by reference for all purposes.

BACKGROUND

1. Field of the Disclosure

The present disclosure relates to a composition for relieving a hangover, more particularly a composition for relieving a hangover including as its active ingredients *Corylus heterophylla* Fisher nut extract, *Alnus japonica* Steud. stem extract and *Sorbus commixta* fruit extract.

2. Description of the Background Art

In drinking, a small dose of the whole alcohol is primarily absorbed through the esophageal mucosa and the oral mucosa. After that, about 90% of it is absorbed in the stomach and then 10% of it is absorbed in the small intestine. Alcohol thus absorbed into the body is excreted by 10% to lungs and in urine and sweat, and metabolized and oxidized in the liver by 90%.

The alcohol transferred in the blood into the liver is metabolized to acetaldehyde by means of the various enzymes produced in the liver and the produced acetaldehyde is metabolized by means again of the enzymes to acetate, which is non-hazardous to human bodies. The acetate is decomposed in the blood to carbon dioxide and water thereafter. Ethanol metabolism in the liver is performed by ADH (alcohol dehydrogenase) and ALDH (acetaldehyde dehydrogenase). ADH is responsible for oxidizing ethanol mainly when concentration of ethanol in the blood is low, whereas it is relatively useless at high ethanol concentration, particularly for long-term ethanol intake.

According to studies on a variety of hangover symptoms, thirst, fatigue and headache are expressed as the effects of residual alcohol while dehydration, internal electrolyte imbalance, gastrointestinal system disorders, hypoglycemia and disorders of sleeping and biorhythms have been reported. Besides, water loss can be accelerated due to vomiting and diarrhea while alcohol can directly damage the stomach walls and the small intestine. Furthermore, alcohol increases production of gastric acid and secretion of pancreastic juice and small intestinal juice, causing epigastrium pains, nausea and vomiting. In addition, hypoglycemia can be brought about by change in metabolic states within the liver and other organs due to alcohol, where both fatty liver caused by alcohol metabolism and lactic acid build-up as the product of intermediary metabolism suppress glucose production. Since glucose is the major energy source for the brain hypoglycemia can have influence on hangover symptoms such as fatigue, lethargy and affective disorders. Meanwhile, alcoholic blackouts arise when alcohol shuts off the activities of specific nerve receptors which imprint new memory onto the brain. (Division of Hygienic Pharmacy of the Korean Association of College of Pharmacy, *The Health Functional Food Study by Disease*, Shinilbooks, 2009, pp. 137-145).

Curcuma longa, pueraria roots, pueraria flowers, chrysanthemums, *Alnus japonica* steud, oriental raisin trees and the like have long been known for their relieving effects of hangovers in *Donguibogam* (Principles and Practice of Eastern Medicine) and the like while asparaginic acid and vitamin C are recognized for their high hangover relieving efficacy. It is written in *Components and Applications of Medicinal Herbs* (By Moon Gwan Shim, 1999, Science Encyclopedia Publishing Company) that tea plants, Potamogeton distinctus A. BENN., iris lacteal Pall., mung beans, Pueraria labata Ohwi, Securinega suffruticosa, oriental raisin trees, water chestnuts and *Amomum cadamomum L.* have hangover relieving effects while it is written in some data of the Information Center for Agriculture and Life Sciences of Seoul National University that spinach and Pueraria labata Ohwi have hangover relieving effects.

*The Health Functional Food Study by Disease* specifies BIOZYME, Phragmitis Rhizoma extract, Mildronate, Liv. 52, Pueraria labata Ohwi, taurine, red koji pigment extract, aloe vera and *ginseng* saponins for which they have evaluated hangover relieving effects.

The inventor of the present disclosure applied on Mar. 19, 1997 his invention of natural tea for relieving a hangover, which has *Alnus japonica* Steud. extract and *Sorbus commixta* extract, as its active ingredients and registered it on Dec. 5, 1998 as Korean Patent Registration No. 181168.

*Alnus japonica* Steud. has been used for detoxifying the liver for hundreds of years and, particularly, is known for its performance of relieving alcohol poisoning because *Alnus japonica* Steud. is a tree species which has significant efficacy of removing hangovers, relieving alcohol addiction and improving liver performance. What is used as medicines are the leaves and sub-branches bark of *Alnus japonica* Steud., which have a characteristic of coolness, taste astringent and spicy and have the effect of reducing temperature and detoxifying. *Alnus japonica* Steud. can help cure hangovers and recover liver functions when its dried sub-branches and bark are drunk.

It is known that *Sorbus commixta* fruits are used for scurvy and cough and are effective against tuberculosis, stroke, hypertension, digestive disorders, neuralgia, rheumatism, arthritis and the like, where its stem bark and fruits are used for medicines because it is known that its bark, leaves, stems and fruits contain ordinary components such as moisture, proteins, carbohydrates and ash contents and various active ingredients as well.

Although *Sorbus commixta* had not been known for its effect of relieving a hangover, the inventor of the present disclosure identified for the first time the mixture of *Alnus japonica* Steud. extract and *Sorbus commixta* extract has an synergistic effect of relieving a hangover and registered his invention of the natural tea for relieving a hangover, which has *Alnus japonica* Steud. extract and *Sorbus commixta* extract as its active ingredients as Korean Patent Registration No. 181168.

Korean Patent Registration No. 181168 discloses in the experimental method "for evaluating the effect of curing a hangover by the natural tea according to the present disclosure, ethyl alcohol decomposition ratios were measured by adding 0.1 liter of the natural tea of the mixing ratio as shown in Table 1 into one liter of ethyl alcohol of 30 and 50%, respectively, at room temperature and under opened and atmospheric conditions. Because alcohol concentrations can be measured by means of an alcoholmeter the present inventor hereby presents the ethyl alcohol decomposition ratios as an index of the effects of the present disclosure."

After registering and during implementing his Korean Patent Registration No. 181168, the inventor of the present disclosure has been checked whether there arise any synergistic effects when extracts of countless edible vegetables plants are mixed with *Alnus japonica* Steud. extract and *Sorbus commixta* extract in order to invent a composition for relieving a hangover which has a hangover relieving effect higher than that of Korean Patent Registration No. 181168. In continuous study according to the experimental method disclosed in Korean Patent Registration No. 181168, he completed the present disclosure by verifying a synergistic effect of a mixture of the *Alnus japonica* Steud. stem extract, the *Sorbus commixta* fruit extract and *Corylus heterophylla* Fisher nut extract.

*Corylus heterophylla* Fisher nuts are collected in fall and dried under the sunlight for use. The nuts are known for their medicinal effects for digestive disorders and chronic large intestinal diseases. in eastern medicinal treatment, it is written that the nuts help easy digestion and are used as appetite stimulating medicines, roborants and antitussive drugs while the ripen nuts are eaten as a fruit like chestnuts or compressed for extracting oil for eating.

Although the hangover relieving effect of *Corylus heterophylla* Fisher has not been known and it has never been even listed as a raw material of a composition for relieving a hangover, the inventor of the present disclosure for the first time identified the synergistic effect of the *Corylus heterophylla* Fisher nut extract of relieving a hangover when they are mixed with the *Alnus japonica* Steud. stem extract and *Sorbus commixta* fruit extract. Its potential was identified according to the experimental method of Korean Patent Registration No. 181168 and, in the present disclosure, its hangover relieving effects were confirmed through in vivo tests (including animal testing and human experiment), which are still more precise than the experimental method disclosed in Korean Patent Registration No. 181168.

RELATED ART DOCUMENTS

Patent Literature (Patent Literature 001) Korean Patent Registration No. 181168, NATURAL TEA FOR RELIEVING HANGOVER AND MANUFACTURING METHOD THEREOF (registered on Dec. 5, 1998).

SUMMARY

The present disclosure is directed to the composition for relieving a hangover which has a hangover relieving effect higher than that of the composition for relieving a hangover including as its active ingredients *Alnus japonica* Steud. extract and *Sorbus commixta* extract as disclosed in Korean Patent Registration No. 181168.

The present disclosure provides the composition for relieving a hangover including as its active ingredients *Corylus heterophylla* Fisher nut extract, *Alnus japonica* Steud. stem extract and *Sorbus commixta* fruit extract, wherein, for 100 wt % of the active ingredients, 50 to 70 wt % of the *Corylus heterophylla* Fisher nut extract, 10 to 20 wt % of the *Alnus japonica* Steud. stem extract and 10 to 30 wt % of the *Sorbus commixta* fruit extract are included.

In addition, the present disclosure provides a health functional food including the composition for relieving a hangover and a sitologically acceptable food material and a food additive, wherein, for the entire weight of the health functional food save for mixing water, 0.1 to 99.9 wt % of the composition for relieving a hangover are included.

In addition, the present disclosure provides the health functional food as a beverage.

It is verified that the composition for relieving a hangover according to the present disclosure has an effect of significantly decreasing blood alcohol concentration and significantly alleviating various hangover symptoms through in vivo tests (including animal testing and human experiment) compared with the composition for relieving a hangover including as its active ingredients *Alnus japonica* Steud. extract and *Sorbus commixta* extract as disclosed in Korean Patent Registration No. 181168.

DETAILED DESCRIPTION

The term of 'to extract/extracting/extraction' used in the present disclosure refers to manipulation to take, using a solvent or a reagent, a specific substance out of a solid or a liquid material. In other words, it refers to manipulation to dissolve or separate only a specific substance in a mixture, for example, extracting a medicinal substance from a plant and the like using water or an organic solvent such as ethanol (ethyl alcohol) and ether.

The term of 'extract' used in the present disclosure refers to a substance separated from a target raw material through the ordinary extracting process, as described above, and includes a liquid extract by using an extractant or its concentrate or its pulverized one. The extract of the present disclosure includes the whole of the extracts which show practically an identical effect by using the extractant as well as any other extractants. The extracting process of the present disclosure can be repeated several times and go through another ordinary concentration process. The extract according to the present disclosure can be manufactured into particles through another process such as vacuum distillation, lyophilization, spray drying and the like.

The present disclosure provides the composition for relieving a hangover including as its active ingredients *Corylus heterophylla* Fisher nut extract, *Alnus japonica* Steud. stem extract and *Sorbus commixta* fruit extract.

The composition according to the present disclosure can include purified water and, besides *Corylus heterophylla* Fisher nut extract, *Alnus japonica* Steud. stem extract and *Sorbus commixta* fruit extract as the active ingredients, edible plant extract such as liquorice and jujubes and honey, the natural sweetener.

The composition for relieving a hangover including as its active ingredients *Corylus heterophylla* Fisher nut extract, *Alnus japonica* Steud. stem extract and *Sorbus commixta* fruit extract according to the present disclosure can be added to a health functional food for the purpose of hangover relieving while the composition for relieving a hangover according to the present disclosure can be used together with food raw materials and food additives when it is added to a food.

According to the Act on Health Functional Food, Article 3, 'a health functional food' refers to a food manufactured (including being processed. The same hereinafter) by using a raw material or a substance having functionality useful to human bodies, where 'functionality' refers to controlling nutrients in relation to the human structure and functions or obtaining an effect useful to health use such as physiological action.

Health functional foods to which the composition for relieving a hangover according to the present disclosure are not specifically limited. The foods can be, for example, beverages, soups, extracts, jellies, candies, chocolates, chewing gums and the like, to which sitologically accepted food additives can be added such as sweeteners, acidulants and flavorings.

The Food Code issued by the Ministry of Food and Drug Safety of Korea sets forth *Alnus japonica* Steud. and *Sorbus commixta* as raw materials limitedly accepted for food. When a raw material which falls under the category limitedly accepted for food is added, the whole quantity of the material to add should be under 50% of the corresponding product (save for mixing water).

When the composition for relieving a hangover according to the present disclosure is added to a food, 0.1 to 99.9 wt %, desirably 1 to 50 wt %, of the composition can be included in the food with reference to the whole quantity of the food (100 wt %) save for mixing water (purified water).

When the food to which the composition of the present disclosure can be added is a beverage, the beverage is not restricted in terms of its ingredients save for the fact that the beverage includes as its active ingredient the composition according to the present disclosure and the beverage can further include food additives such as purified water, sweeteners, acidulants and flavorings like ordinary beverages.

Components of the composition according to the present disclosure are as follows, as listed in Table 1.

TABLE 1

| Component | | Composition ratio (wt %) |
|---|---|---|
| Component 1 | *Corylus heterophylla* Fisher nut extract | 50-70 |
| Component 2 | *Alnus japonica* Steud. stem extract | 10-20 |
| Component 3 | *Sorbus commixta* fruit extract | 10-30 |

When the composition ratio (content) of each of the components falls short of the range, sufficient hangover relieving cannot be expected whereas, when it exceeds the range, there occurs an adverse effect to hangover relieving and it is not desirable in that it is not harmonized with other extracts in terms of taste. (Refer to Tables 3, 4, 6 and 7).

The Supreme Court of Korea decided that "in the case an invention of a registered patent expresses numerically limit the range of a subject matter of another patent publicly known before the invention was applied, when the objectives and effects of the patented invention are extended from the publicly known patent with only difference between them in whether numerical limitation, if there arises no significant difference of effects near the limited numerical range the patented invention is nothing more than simple numerical limitation a person skilled in the art can appropriately select through ordinary and repeated experiments, thereby repudiating its inventive step. However, when the numerical limitation is just a complementary matter of the patented invention in that another subject matter is added so that inventive steps of the patented invention should be acknowledged, or when, even if the compositions of both of the inventions are identical save for the numerical limitation, the numerical limitation is significant as a technological tool for achieving an objective different from that of the publicly known invention and its effects are also different from those of the publicly known invention, the inventive steps of the patented invention shall not be denied by reason of the fact the numerical limitation has no critical significance." (The Supreme Court of Korea, as announced on Aug. 19, 2008 2008HU4998 Decision).

In the present disclosure, the *Corylus heterophylla* Fisher nut extract as a publicly unknown subject matter is added to the *Alnus japonica* Steud. stem extract and the *Sorbus commixta* fruit extract as publicly known subject matters. Therefore, the inventive step of the present disclosure should not be repudiated by reason that there is no critical significance of numerical limitation. However, the present disclosure presents animal testing and human experiment data around the range of its numerical limitation.

<Embodiment 1> Manufacture of the *Corylus heterophylla* Fisher Nut Extract 1-1. *Corylus heterophylla* Fisher nuts were collected, dried and milled. The milled nuts were immersed in 80% ethanol and extracted for 12 hours at 70° C. After that, extraction debris was removed, concentrated under reduced pressure and dried, thereby producing *Corylus heterophylla* Fisher nut extract in the shape of particles.

1-2. *Corylus heterophylla* Fisher nuts were collected, dried and milled. The milled nuts were immersed in hot water at 70° C. and extracted for 12 hours at 80-95° C. After that, extraction debris was removed, concentrated under reduced pressure and dried, thereby producing *Corylus heterophylla* Fisher nut extract in the shape of particles.

<Embodiment 2> Manufacture of the *Alnus japonica* Steud. Stem Extract 2-1. *Alnus japonica* Steud. stems were collected, dried and milled. The milled stems were immersed in 80% ethanol and extracted for 12 hours at 70° C. After that, extraction debris was removed, concentrated under reduced pressure and dried, thereby producing *Alnus japonica* Steud. stem extract in the shape of particles.

2-2. *Alnus japonica* Steud. stems were collected, dried and milled. The milled stems were immersed in hot water at 70° C. and extracted for 12 hours at 80-95° C. After that, extraction debris was removed, concentrated under reduced pressure and dried, thereby producing *Alnus japonica* Steud. stem extract in the shape of particles.

<Embodiment 3> Manufacture of the *Sorbus commixta* Fruit Extract 3-1. *Sorbus commixta* fruit was collected, dried and milled. The milled fruit was immersed in 80% ethanol and extracted for 12 hours at 70° C. After that, extraction debris was removed, concentrated under reduced pressure and dried, thereby producing *Sorbus commixta* fruit extract in the shape of particles.

3-2. *Sorbus commixta* fruit was collected, dried and milled. The milled fruit was immersed in hot water at 70° C. and extracted for 12 hours at 80-95° C. After that, extraction debris was removed, concentrated under reduced pressure and dried, thereby producing *Sorbus commixta* fruit extract in the shape of particles.

<Embodiment 4> Manufacture of the Liquid Composition 4-1. For animal testing, the composition according to the present disclosure was manufactured into liquid by adding 1,000 cc of distilled water to 100 g of the composition according to the composition ratios of embodiments 'a' through 'e' and comparative examples 'a' through 'f' as listed in Table 2.

4-2. For human experiment, the composition according to the present disclosure was manufactured into liquid by adding 1,000 cc of distilled water to 100 g of the composition according to the composition ratios of embodiments 'a' through 'e' and comparative examples 'a' through 'f' as listed in Table 2 and mixing 80 wt % of the produced liquid composition with 20 wt % of honey.

TABLE 2

|  |  | Corylus heterophylla Fisher nut extract | Alnus japonica Steud. stem extract | Sorbus commixta fruit extract |
|---|---|---|---|---|
| Embodiments | a | 70 | 10 | 20 |
|  | b | 70 | 20 | 10 |
|  | c | 60 | 10 | 30 |
|  | d | 60 | 20 | 20 |
|  | e | 50 | 20 | 30 |
| Comparative examples | a | 80 | 10 | 10 |
|  | b | 40 | 20 | 40 |
|  | c | — | 30 | 70 |
|  | d | — | 40 | 60 |
|  | e | — | 50 | 50 |
|  | f | — | 60 | 40 |

(unit: wt %)

<Experimental Example 1> Animal Testing

Animal testing were referred to the Prof. Jong-Dae Kim's team of Department of Food Science & Biotechnology, College of Agriculture and Life Sciences, Kangwon National University and carried out there.

1-1. Test Description
Animal to test: Ten male white rats (about 260 g per rat) were deployed in each treatment group.
Control group: Groups were administered 11 specimens of the liquid compositions.
Test spiritus: Chivas Regal (alcohol concentration: 40%)
Ethanol administration dose: Single acute ethanol intoxication dose (4 g ethanol/1 kg body wt.)
Liquid composition specimen administration dose: 2.5 g per 1 kg of body weight
Blood drawing interval: 60, 90, 150 and 240 minutes after alcohol administration
Specimen analyzed: Blood was drawn from eyeballs and serum was separated.
Analysis method: Blood alcohol concentrations were analyzed according to the enzyme method.

1-2. Test Animals and their Treatment
For the tests, postnatal white male Sprague Dawley rats (250 to 260 g of body weight per rat) were purchased from Daehan Biolink Co. Ltd. and adapted for 1 week at Kangwon National University Laboratory Animal Centre (22±2° C. of temperature; 50 to 55% of humidity; and 12-hour light/dark cycle regime). For the entire period of the tests the rats were provided with water and feed in unrestricted quantity.

Ten of the adapted rats were distributed to each of the treatment groups. Chivas Regal (alcohol concentration: 40%) as test spritus was orally administered to the rats with reference to their body weight. The liquid composition specimens of Embodiment 4-1 were orally administered 30 minutes before or after ethanol administration.

1-3. $1_{st}$ Test (Pre-Treatment)
The liquid composition specimens were administered 30 minutes prior to alcohol administration and blood alcohol concentration was measured by drawing blood subsequent to 60, 90, 150 and 240 minutes after alcohol administration.

1-4. $2^{nd}$ Test (Post-Treatment)
Was performed 3 weeks after the $1^{st}$ test was completed, where the liquid composition specimens were administered 30 minutes after alcohol administration and blood alcohol concentration was measured by drawing blood 90, 150 and 240 minutes after alcohol administration.

1-5. Blood Alcohol Concentration Analyses
Blood was collected from eyeballs 60, 90, 150 and 240 min. after alcohol administration and put into a serum separation tube for serum separation by centrifugation (15,000 rpm, 10 min, 4° C.). Alcohol content was measured with an alcohol assay kit (Komabiotech, Korea). 2× yellow reaction mixture (90 μl) was added to the separated serum (10 μl). After being placed for incubation for 30 min, at 37° C., the expressed color formation was measured at 570 nm.

Alcohol concentration (mM) was measured by putting measured light absorbance into the standard alcohol curve. For the standard curve, absorbance was measured according to the same method as above by diluting 10 mM of standard solution to 2,000, 1,000, 500, 250, 125, 62.5, 31.25, and 0 μM.

1-6. Statistical Analyses
Test results were expressed by mean and standard deviation values (mean±SD) and statistical significance among the experimental groups was investigated (P<0.05) according to the one-way ANOVA test (Bonferroni test for post hoc multiple comparison) with GraphPad InStat software.

1-7. Results of the $1^{st}$ Test (Specimen Administration 30 Minutes Before Alcohol Administration) are as Follows, as Listed in Table 3.

TABLE 3

|  |  | Composition (wt %) | | | BAC (mean ± SD) (μM) | | | |
|---|---|---|---|---|---|---|---|---|
|  |  | C. extract | A. extract | S. extract | 60 min after AA | 90 min after AA | 150 min after AA | 240 min after AA |
| EM | a | 70 | 10 | 20 | 579 ± 52 | 442 ± 38 | 323.6 ± 26 | 315 ± 35 |
|  | b | 70 | 20 | 10 | 464 ± 37 | 389 ± 39 | 385 ± 40 | 310 ± 44 |
|  | c | 60 | 10 | 30 | 576.3 ± 122 | 477.9 ± 37 | 308.5 ± 50 | 309.7 ± 62 |
|  | d | 60 | 20 | 20 | 471 ± 21 | 459 ± 20 | 415 ± 16 | 389 ± 20 |
|  | e | 50 | 20 | 30 | 597.8 ± 53 | 492.1 ± 117 | 437.4 ± 76 | 415.7 ± 70 |
| CE | a | 80 | 10 | 10 | 686 ± 100 | 568.3 ± 78 | 498.6 ± 81 | 442.8 ± 54 |
|  | b | 40 | 20 | 40 | 671.4 ± 29 | 622.3 ± 27 | 571.3 ± 34 | 549.6 ± 37 |
|  | c | — | 30 | 70 | 656 ± 53 | 648 ± 54 | 588 ± 53 | 568 ± 53 |
|  | d | — | 40 | 60 | 692.8 ± 40 | 669.4 ± 111 | 592.4 ± 116 | 542.3 ± 80 |
|  | e | — | 50 | 50 | 695.5 ± 43 | 582.9 ± 55 | 579.8 ± 60 | 535.7 ± 56 |
|  | f | — | 60 | 40 | 673 ± 89 | 669 ± 89 | 609 ± 87 | 581 ± 85 |

When comparing Embodiment(EM)s 'a' through 'e' according to the present disclosure with Comparative example(CE)s 'a' and 'b' with composition ratios that are not included in EMs of the present disclosure, EMs of the present disclosure to which the liquid composition specimens were administered 30 minutes before alcohol administration (AA) showed blood alcohol concentration(BAC) from 60 minutes after AA decreased lower than that of CEs as follows: 11.0% minimum (EM 'e'/CE 'b'=597.8/671.4) and 32.4% maximum (EM 'b'/CE 'a'=464/686) 60 min after AA; 13.4% min (EM 'e'/CE 'a'=492.1/568.3) and 37.5% max (Em 'b'/CE 'b'=389/622.3) 90 min after AA; 12.3% min (EM 'e'/CE 'a'=437.4/498.6) and 46.0% max (EM 'c'/CE 'b'=308.5/571.3) 150 min after AA; and min 6.1% (EM 'e'/CE 'a'=415.7/442.8) and 43.6% max (EM 'c'/CE 'b'=309.7/549.6) 240 min after AA.

When comparing EMs 'a' and 'b' according to the present disclosure with CEs 'c' through 'f' including only *Alnus japonica* Steud. stem extract and *Sorbus commixta* fruit extract as in Korean Patent Registration No. 181168, EMs of the present disclosure to which the liquid composition specimens were administered 30 minutes before AA showed BAC from 60 minutes after AA decreased lower than that of CEs as follows: 8.9% min (EM 'e'/CE 'c'=597.8/656) and 33.3% max (EM 'b'/CE 'e'=464/695.5) 60 min after AA; 15.6% min (EM 'e'/CE 'e'=492.1/582.9) and 41.9% max (EM 'b'/CE 'd'=389/669.4) 90 min after AA; 24.6% min (EM 'e'/CE 'e'=437.4/579.8) and 49.3% max (EM 'c'/CE 'f'=308.5/609) 150 min after AA; and 22.4% min (EM 'e'/CE 'e'=415.7/535.7) and 46.7% max (EM 'c'/CE 'f'=309.7/581) 240 min after AA.

When EMs 'a' through 'e' according to the present disclosure compared with CE 'd' whose composition ratio is closest to that of Dawn 808 the Hangover Solution currently on the market by implementing Korean Patent Registration No. 181168, EMs of the present disclosure to which the liquid composition specimens were administered 30 minutes before AA showed BAC from 60 minutes after AA decreased lower than that of CE as follows: 13.7% min (EM 'e'/CE 'd'=597.8/692.8) and 33.0% max (EM 'b'/CE 'd'=464/692.8) 60 min after AA; 26.5% min (EM 'e'/CE 'd'=492.1/669.4) and 41.9% max (EM 'b'/CE 'd'=389/669.4) 90 min after AA; 26.2% min (EM 'e'/CE 'd'=437.4/592.4) and 48.0% max (EM 'c'/CE 'd'=308.5/592.4) 150 min after AA; and min 23.3% (EM 'e'/CE 'd'=415.7/542.3) and 42.9% max (EM 'c'/CE 'd'=309.7/542.3) 240 min after AA.

1-8. Results of the $2^{nd}$ Test (Specimen Administration 30 Minutes after Alcohol Administration) are as Follows, as Listed in Table 4.

TABLE 4

| | | Composition (wt %) | | | BAC (mean ± SD) (μM) | | |
|---|---|---|---|---|---|---|---|
| | | C. extract | A. extract | S. extract | 90 min after AA | 150 min after AA | 240 min after AA |
| EM | a | 70 | 10 | 20 | 567 ± 45 | 501 ± 32 | 399 ± 62 |
| | b | 70 | 20 | 10 | 458 ± 45 | 416 ± 35 | 360 ± 39 |
| | c | 60 | 10 | 30 | 451 ± 53 | 426 ± 49 | 301 ± 51 |
| | d | 60 | 20 | 20 | 476 ± 48 | 434 ± 44 | 387 ± 39 |
| | e | 50 | 20 | 30 | 546 ± 42 | 504 ± 45 | 455 ± 48 |
| CE | a | 80 | 10 | 10 | 605 ± 57 | 537 ± 60 | 470 ± 56 |
| | b | 40 | 20 | 40 | 588 ± 45 | 544 ± 46 | 504 ± 50 |
| | c | — | 30 | 70 | 643 ± 50 | 601 ± 53 | 551 ± 56 |
| | d | — | 40 | 60 | 628 ± 90 | 586 ± 94 | 567 ± 97 |
| | e | — | 50 | 50 | 614 ± 57 | 571 ± 57 | 540 ± 51 |
| | f | — | 60 | 40 | 613 ± 87 | 524 ± 75 | 514 ± 74 |

When comparing EMs 'a' through 'e' according to the present disclosure with CEs 'a' and 'b' with composition ratios that are not included in EMs of the present disclosure, EMs of the present disclosure to which the liquid composition specimens were administered 30 minutes after AA showed BAC from 90 minutes after AA decreased lower than that of CEs as follows: 3.6% min (EM 'a'/CE 'b'=567/588) and 25.5% max (EM 'c'/CE 'a'=451/605) 90 min after AA; 6.1% min (EM 'e'/CE 'a'=504/537) and 23.5% max (EM 'b'/CE b=416/544) 150 min after AA; and 3.2% min (EM 'e'/CE 'a'=455/470) and 40.3% max (EM 'c'/CE 'b'=301/504) 240 min after AA.

When comparing EMs 'a' through 'e' according to the present disclosure with CEs 'c' through f including only *Alnus japonica* Steud. stem extract and *Sorbus commixta* fruit extract as in Korean Patent Registration No. 181168, EMs of the present disclosure to which the liquid composition specimens were administered 30 minutes after AA showed BAC from 90 minutes after AA decreased lower than that of CEs as follows: min 7.5% (EM 'a'/CE 'f'=567/613) and 29.9% max (EM 'c'/CE 'c'=451/643) 90 min after AA; 3.8% min (EM 'e'/CE 'f'=504/524) and 30.8% max (EM 'b'/CE 'c'=416/601) 150 min after AA; and 11.5% min (EM 'e'/CE 'f'=455/514) and 46.9% max (EM 'c'/CE 'd'=301/567) 240 min after AA.

When EMs 'a' through 'e' according to the present disclosure compared with CE 'd' whose composition ratio is closest to that of Dawn 808 the Hangover Solution currently on the market by implementing Korean Patent Registration No. 181168, EMs of the present disclosure to which the liquid composition specimens were administered 30 minutes after AA showed BAC from 90 minutes after AA decreased lower than that of CE as follows: 9.7% min (EM 'a'/CE 'd'=567/628) and 28.2% (EM 'c'/CE 'd'=451/628) 90 min after AA; 14.0% min (EM 'e'/CE 'd'=504/586) and 29.0% max (EM 'b'/CE 'd'=416/586) 150 min after AA; and 19.8% min (EM 'e'/CE 'd'=455/567) and 46.9% max (EM 'c'/CE 'd'=301/567) 240 min after AA.

<Experimental Example 2> Human Experiment

For human experiment, human subjects stayed in the patient rooms of Seoul Surgery Clinic in Dongsong-eup, Cheolwon-gun, Gangwon-do, Korea after giving their consent. They administered the liquid composition specimens before ethanol administration or after ethanol administration completion. Their blood was drawn by nurses after ethanol administration completion by time and BAC measurement was referred to Green Cross Corp.

2-1. Test Description
Human subjects: as listed in Table 5

TABLE 5

|  |  | Participants | | | |
|---|---|---|---|---|---|
|  |  | Sex | Name | Age (yrs) | Weight (kg) |
| EM | a | M | Han ** | 33 | 54 |
|  | b | M | Lee ** | 36 | 90 |
|  | c | M | Kim ** | 38 | 57 |
|  | d | M | Kim ** | 34 | 67 |
|  | e | M | Lee ** | 39 | 90 |
| CE | a | M | Park ** | 39 | 93 |
|  | b | M | Lim ** | 50 | 66 |
|  | c | M | Jo ** | 38 | 65 |
|  | d | M | Yu ** | 39 | 77 |
|  | e | M | Song ** | 47 | 88 |
|  | f | M | Kim ** | 43 | 71 |

After quitting alcohol administration for 3 days, they commenced it at 6 PM: drinking continued for 30 minutes with munchies of 170 g of jerky and 200 g of peaches. AA: 3 g of Chivas Regal (alcohol concentration: 40%) per 1 kg of body weight 2.5 g of the liquid composition specimen of Embodiment 4-2 was administered per 1 kg of body weight. Blood drawing interval: 60, 90, 150 and 240 minutes after AA 2-2. $1^{st}$ Test
The liquid composition specimens were administered 30 minutes prior to alcohol administration and blood alcohol concentration was measured by drawing blood subsequent to 60, 90, 150 and 240 minutes after alcohol administration.

2-3. $2^{nd}$ Test
Was performed 3 days without AA after the $1^{st}$ test was completed, where the liquid composition specimens were administered 30 minutes after AA completion (AAC) and BAC was measured by drawing blood 90, 150 and 240 minutes after AAC.

2-4. Results of the $1^{st}$ Test (Specimen Administration 30 Minutes Before AA) are as Follows, as Listed in Table 6.

TABLE 6

|  |  | Composition (wt %) | | | BAC, % | | | |
|---|---|---|---|---|---|---|---|---|
|  |  | C. ex-tract | A. ex-tract | S. ex-tract | 60 min after AAC | 90 min after AAC | 150 min after AAC | 240 min after AAC |
| EM | a | 70 | 10 | 20 | 0.118 | 0.090 | 0.048 | 0.020 |
|  | b | 70 | 20 | 10 | 0.112 | 0.073 | 0.030 | 0.013 |
|  | c | 60 | 10 | 30 | 0.100 | 0.051 | 0.022 | 0.011 |
|  | d | 60 | 20 | 20 | 0.107 | 0.064 | 0.024 | 0.012 |
|  | e | 50 | 20 | 30 | 0.115 | 0.079 | 0.045 | 0.019 |
| CE | a | 80 | 10 | 10 | 0.127 | 0.096 | 0.058 | 0.039 |
|  | b | 40 | 20 | 40 | 0.118 | 0.090 | 0.048 | 0.027 |
|  | c | — | 30 | 70 | 0.127 | 0.101 | 0.067 | 0.047 |
|  | d | — | 40 | 60 | 0.126 | 0.099 | 0.060 | 0.040 |
|  | e | — | 50 | 50 | 0.120 | 0.098 | 0.050 | 0.030 |
|  | f | — | 60 | 40 | 0.125 | 0.094 | 0.061 | 0.045 |

When comparing EMs 'a' through 'e' according to the present disclosure with CEs 'a' and 'b' with composition ratios that are not included in EMs of the present disclosure, EMs of the present disclosure to which the liquid composition specimens were administered 30 minutes before AA showed BAC from 60 minutes after AAC decreased lower than that of CEs as follows: 21.3% max (EM 'c'/CE 'a'=0.100/0.127) 60 min after AAC; 46.9% max (EM 'c'/CE 'a'=0.051/0.096) 90 min after AAC; 62.1% max (EM 'c'/CE 'a'=0.022/0.058) 150 min after AAC; and 25.9% min (EM 'a'/CE 'b'=0.020/0.027) and 71.8% max (EM 'c'/CE 'a'=0.011/0.039) 240 min after AAC.

When comparing EMs a through e according to the present disclosure with CEs c through f including only *Alnus japonica* Steud. stem extract and *Sorbus commixta* fruit extract as in Korean Patent Registration No. 181168, EMs of the present disclosure to which the liquid composition specimens were administered 30 minutes before AA showed BAC from 60 minutes after AAC decreased lower than that of CEs as follows: 1.7% min (EM 'a'/CE 'e'=0.118/0.120) and 21.3% max (EM 'c'/CE 'c'=0.100/0.127) 60 min after AAC; 4.3% min (EM 'a'/CE 'f'=0.090/0.094) and 49.5% max (EM 'c'/CE 'c'=0.051/0.101) 90 min after AAC; 4.0% min (EM 'a'/CE 'e'=0.048/0.050) and 67.2% max (EM 'c'/CE 'c'=0.022/0.067) 150 min after AAC; and 33.3% min (EM 'a'/CE 'e'=0.020/0.030) and 76.6% max (EM 'c'/CE 'c'=0.011/0.047) 240 min after AAC.

When EMs 'a' through 'e' according to the present disclosure compared with CE 'd' whose composition ratio is closest to that of Dawn 808 the Hangover Solution currently on the market by implementing Korean Patent Registration No. 181168, EMs of the present disclosure to which the liquid composition specimens were administered 30 minutes before AA showed BAC from 60 minutes after AAC decreased lower than that of CE as follows: 6.3% min (EM 'a'/CE 'd'=0.118/0.126) and 20.6% max (EM 'c'/CE 'd'=0.100/0.126) 60 min after AAC; 9.1% min (EM 'a'/CE 'd'=0.090/0.099) and 48.5% max (EM 'c'/CE 'd'=0.051/0.099) 90 min after AAC; 20% min (EM 'a'/CE 'd'=0.048/0.060) and 63.3% (EM 'c'/CE 'd'=0.022/0.060) 150 min after AAC; and 50.0% min (EM 'a'/CE 'd'=0.020/0.040) and 72.5% max (EM 'c'/CE 'd'=0.011/0.040) 240 min after AAC.

2-4. Results of the $2^{nd}$ Test (Specimen Administration 30 Minutes after AAC) are as Follows, as Listed in Table 7.

TABLE 7

|  |  | Composition (wt %) | | | BAC (%) | | |
|---|---|---|---|---|---|---|---|
|  |  | C. ex-tract | A. ex-tract | S. ex-tract | 90 min after AAC | 150 min after AAC | 240 min after AAC |
| EM | a | 70 | 10 | 20 | 0.094 | 0.050 | 0.025 |
|  | b | 70 | 20 | 10 | 0.080 | 0.032 | 0.019 |
|  | c | 60 | 10 | 30 | 0.065 | 0.024 | 0.014 |
|  | d | 60 | 20 | 20 | 0.072 | 0.026 | 0.017 |
|  | e | 50 | 20 | 30 | 0.088 | 0.045 | 0.023 |
| CE | a | 80 | 10 | 10 | 0.101 | 0.067 | 0.038 |
|  | b | 40 | 20 | 40 | 0.097 | 0.052 | 0.029 |
|  | c | — | 30 | 70 | 0.109 | 0.069 | 0.047 |
|  | d | — | 40 | 60 | 0.104 | 0.065 | 0.033 |
|  | e | — | 50 | 50 | 0.101 | 0.054 | 0.030 |
|  | f | — | 60 | 40 | 0.106 | 0.067 | 0.049 |

When comparing EMs 'a' through 'e' according to the present disclosure with CEs 'a' and 'b' with composition ratios that are not included in EMs of the present disclosure, EMs of the present disclosure to which the liquid composition specimens were administered 30 minutes after AA showed BAC from 90 minutes after AAC decreased lower than that of CEs as follows: 3.1% min (EM 'a'/CE 'b'=0.094/0.097) and 35.6% (EM 'c'/CE 'a'=0.065/0.101) 90 min after AAC; 3.8% min (EM 'a'/CE 'b'=0.050/0.052) and 64.2% max (EM 'c'/CE 'a'=0.024/0.067) 150 min after AAC; and 13.8% (EM 'a'/CE 'b'=0.025/0.029) and 63.2% max (EM 'c'/CE 'a'=0.014/0.038) 240 min after AAC).

When comparing EMs 'a' through 'e' according to the present disclosure with CEs 'c' through 'f' including only *Alnus japonica* Steud. stem extract and *Sorbus* commixta fruit extract as in Korean Patent Registration No. 181168, EMs of the present disclosure to which the liquid composition specimens were administered 30 minutes after before AA showed BAC from 90 minutes after AAC decreased lower than that of CEs as follows: 6.9% min (EM 'a'/CE 'e'=0.094/0.101) and 40.4% max (EM 'c'/CE 'c'=0.065/0.109) 90 min after AAC; 7.4% min (EM 'a'/CE 'e'=0.050/0.054) and 65.2% (EM 'c'/CE 'c'=0.024/0.069) 150 min after AAC; and 16.7% min (EM 'a'/CE 'e'=0.025/0.030) and 71.4% max (EM 'c'/CE 'f'=0.014/0.049) 240 min after AAC).

When EMs 'a' through 'e' according to the present disclosure compared with CE 'd' whose composition ratio is closest to that of Dawn 808 the Hangover Solution currently on the market by implementing Korean Patent Registration No. 181168, EMs of the present disclosure to which the liquid composition specimens were administered 30 minutes after AA showed BAC from 90 minutes after AAC decreased lower than that of CE as follows: 9.6% min (EM 'a'/CE 'd'=0.094/0.104) and 37.5% (EM 'c'/CE 'd'=0.065/0.104) 90 min after AAC; 23.1% min (EM 'a'/CE 'd'=0.050/0.065) and 63.1% max (EM 'c'/CE 'd'=0.024/0.065) 150 min after AAC; and 24.2% min (EM 'a'/CE 'd'=0.025/0.033) and 57.6% max (EM 'c'/CE 'd'=0.014/0.033) 240 min after AAC.

<Experimental Example 3> Survey for Evaluating Hangover Alleviation Effects

Questionnaires were distributed to the test participants at 9 AM the day after the human experiment was performed for evaluating the effects.

3-1. Evaluation of Hangover Alleviation Effects

Each of the questionnaires presented 7 questions including dizziness alleviation effect, thirsty alleviation effect, fatigue alleviation effect, attention disorder alleviation effect, drowsiness alleviation effect, headache alleviation effect and vomiting alleviation effect and let the participants evaluate the effects on a scale of 1 to 5 (very strong effect=5; moderately strong effect=4; moderate effect=3; moderately week effect=2; and very week effect=1).

3-2. $1^{st}$ Questionnaire

The questionnaire was distributed to the test participants at 9 AM the day after the $1^{st}$ clinical test (specimens administration 30 min before AA) were performed for evaluating the effects.

3-3. $2^{nd}$ Questionnaire

The questionnaire was distributed to the test participants at 9 AM the day after the $2^{nd}$ clinical test (specimens administration 30 min after AAC) were performed for evaluating the effects.

3-4. Results of the $1^{st}$ Questionnaire are as Follows as Listed in Table 8.

TABLE 8

| | | Hangover alleviation effects (scores of the questionnaire) | | | | | | | |
|---|---|---|---|---|---|---|---|---|---|
| | | Dizziness alleviation | Thirsty alleviation | Fatigue alleviation | Attention disorder alleviation | Drowsiness alleviation | Headache alleviation | Vomiting alleviation | Mean |
| EM | a | 4 | 4 | 4 | 4 | 4 | 3 | 4 | 3.86 |
| | b | 4 | 5 | 4 | 4 | 4 | 4 | 4 | 4.14 |
| | c | 4 | 5 | 4 | 4 | 4 | 5 | 5 | 4.43 |
| | d | 4 | 5 | 4 | 4 | 4 | 4 | 4 | 4.14 |
| | e | 4 | 4 | 4 | 4 | 4 | 4 | 4 | 4.00 |
| CE | a | 3 | 3 | 3 | 3 | 3 | 3 | 3 | 3.00 |
| | b | 3 | 4 | 4 | 3 | 3 | 3 | 3 | 3.29 |
| | c | 3 | 3 | 3 | 2 | 3 | 3 | 3 | 2.86 |
| | d | 3 | 3 | 3 | 3 | 3 | 3 | 3 | 3.00 |
| | e | 3 | 3 | 3 | 3 | 3 | 4 | 3 | 3.14 |
| | f | 3 | 2 | 3 | 3 | 3 | 3 | 3 | 2.86 |

When the hangover alleviation effects of EMs 'a' through 'e' according to the present disclosure with CEs 'a' and 'b' with composition ratios that are not included in EMs of the present disclosure, CEs 'a' and 'b' scored 3.00 to 3.29 of the full scores of 5 while EMs of the present disclosure scored 3.86 to 4.43 on the same scale.

When the hangover alleviation effects of EMs 'a' through 'e' according to the present disclosure with CEs 'c' through f including only *Alnus japonica* Steud. stem extract and *Sorbus commixta* fruit extract as in Korean Patent Registration No. 181168, CEs 'c' through f scored 2.86 to 3.14 of the full scores of 5 while EMs of the present disclosure scored 3.86 to 4.43 on the same scale.

When the hangover alleviation effects of EMs 'a' through 'e' according to the present disclosure with CE 'd' whose composition ratio is closest to that of Dawn 808 the Hangover Solution currently on the market by implementing Korean Patent Registration No. 181168, CE 'd' scored 3.00 of the full score of 5 while EMs of the present disclosure scored 3.86 to 4.43 on the same scale.

3-5. Results of the 2$^{nd}$ Questionnaire are as Follows as Listed in Table 9.

TABLE 9

| | | Hangover alleviation effects (point(s) of the questionnaire) | | | | | | | |
|---|---|---|---|---|---|---|---|---|---|
| | | Dizziness alleviation | Thirsty alleviation | Fatigue alleviation | Attention disorder alleviation | Drowsiness alleviation | Headache alleviation | Vomiting alleviation | Mean |
| EM | a | 4 | 4 | 3 | 4 | 4 | 3 | 4 | 3.71 |
| | b | 4 | 4 | 4 | 4 | 4 | 4 | 4 | 4.00 |
| | c | 4 | 5 | 4 | 4 | 4 | 4 | 4 | 4.14 |
| | d | 4 | 4 | 4 | 4 | 4 | 4 | 4 | 4.00 |
| | e | 4 | 4 | 4 | 4 | 4 | 3 | 4 | 3.86 |
| CE | a | 3 | 3 | 3 | 3 | 3 | 3 | 3 | 3.00 |
| | b | 3 | 4 | 3 | 3 | 3 | 3 | 3 | 3.14 |
| | c | 3 | 3 | 3 | 2 | 3 | 3 | 3 | 2.86 |
| | d | 3 | 3 | 3 | 3 | 3 | 3 | 3 | 3.00 |
| | e | 3 | 3 | 3 | 3 | 3 | 3 | 3 | 3.00 |
| | f | 3 | 3 | 3 | 3 | 3 | 3 | 2 | 2.86 |

When the hangover alleviation effects of EMs 'a' through 'e' according to the present disclosure with CEs 'a' and 'b' with composition ratios that are not included in EMs of the present disclosure, CEs 'a' and 'b' scored 3.00 to 3.14 of the full scores of 5 while EMs of the present disclosure scored 3.71 to 4.14 on the same scale.

When the hangover alleviation effects of EMs 'a' through 'e' according to the present disclosure with CEs 'c' through 'f' including only *Alnus japonica* Steud. stem extract and *Sorbus commixta* fruit extract as in Korean Patent Registration No. 181168, CEs 'c' through 'f' scored 2.86 to 3.00 of the full scores of 5 while EMs of the present disclosure scored 3.71 to 4.14 on the same scale.

When the hangover alleviation effects of EMs 'a' through 'e' according to the present disclosure with CE 'd' whose composition ratio is closest to that of Dawn 808 the Hangover Solution currently on the market by implementing Korean Patent Registration No. 181168, CE 'd' scored 3.00 of the full score of 5 while EMs of the present disclosure scored 3.71 to 4.14 on the same scale.

What is claimed is:

1. A composition for relieving a hangover comprising an effective amount of a synergistic combination of extracts consisting of:

(a) 50-60% *Corylus heterophylla* Fisher nut extract produced by immersing dried, milled *Corylus heterophylla* Fisher nuts in hot water at 70° C., extracting for 12 hours at 80° C.-95° C., removing *Corylus heterophylla* Fisher nut extraction debris, concentrating under reduced pressure and drying the *Corylus heterophylla* Fisher nut extract;

(b) at least 10% *Alnus japonica* Steud. stem extract produced by immersing dried, milled *Alnus japonica* Steud. stems in hot water at 70° C. and extracting for 12 hours at 80° C.-95° C., removing *Alnus japonica* Steud. stem extraction debris, concentrating under reduced pressure and drying the *Alnus japonica* Steud. stem extract; and (c) 10-30% *Sorbus commixta* fruit extract produced by immersing dried, milled Sorbus commixta fruit in hot water at 70° C. and extracting for 12 hours at 80° C.-95° C., removing *Sorbus commixta* fruit extraction debris, concentrating under reduced pressure and drying the *Sorbus commixta* fruit extract.

* * * * *